United States Patent
Hemert et al.

(10) Patent No.: US 11,259,696 B2
(45) Date of Patent: Mar. 1, 2022

(54) IMAGING OF THE EYE

(71) Applicant: OPTOS PLC, Dunfermline (GB)

(72) Inventors: Jano Van Hemert, Edinburgh (GB); Michael Verhoek, Edinburgh (GB)

(73) Assignee: OPTOS PLC, Dunfermline (GB)

( * ) Notice: Subject to any disclaimer, the term of this patent is extended or adjusted under 35 U.S.C. 154(b) by 339 days.

(21) Appl. No.: 16/438,298

(22) Filed: Jun. 11, 2019

(65) Prior Publication Data

US 2019/0290119 A1    Sep. 26, 2019

Related U.S. Application Data (63) Continuation of application No. 15/484,935, filed on Apr. 11, 2017, now Pat. No. 10,357,150, which is a (Continued)

(30) Foreign Application Priority Data

May 2, 2013    (GB) ...................................... 1307990

(51) Int. Cl.
   G06K 9/00    (2006.01)
   A61B 3/00    (2006.01)
   (Continued)

(52) U.S. Cl.
   CPC .......... *A61B 3/0025* (2013.01); *A61B 3/1005* (2013.01); *A61B 3/1025* (2013.01);
   (Continued)

(58) Field of Classification Search
   None
   See application file for complete search history.

(56) References Cited

U.S. PATENT DOCUMENTS

| | | | |
|---|---|---|---|
| 5,106,183 A | 4/1992 | Yoder, Jr. | |
| 5,159,361 A | 10/1992 | Gambier et al. | |
| (Continued) | | | |

FOREIGN PATENT DOCUMENTS

| | | |
|---|---|---|
| JP | 2000-210260 A | 8/2000 |
| JP | 2010-508932 A | 3/2010 |
| WO | 2008/005611 A2 | 5/2008 |

OTHER PUBLICATIONS

Dobler et al., "Precise modelling of the eye for proton therapy of intra-ocular tumours" (Year: 2002).*

(Continued)

*Primary Examiner* — Soo Jin Park
(74) *Attorney, Agent, or Firm* — DeLucia, Mlynar & Associates LLP (57) ABSTRACT

A method of determining a geometrical measurement of a retina of an eye, comprising obtaining a two dimensional representation of at least a portion of the retina of the eye (34), deriving a geometrical remapping which converts the two dimensional representation of the retinal portion to a three dimensional representation of the retinal portion (36), using one or more coordinates of the two dimensional representation of the retinal portion to define the geometrical measurement to be taken of the retina on the two dimensional representation (38), using the geometrical remapping to convert the or each coordinate of the two dimensional representation of the retinal portion to an equivalent coordinate of the three dimensional representation of the retinal portion (40), and using the or each equivalent coordinate of the three dimensional representation of the retinal portion to determine the geometrical measurement of the retina of the eye (42).

28 Claims, 2 Drawing Sheets

Related U.S. Application Data continuation of application No. 14/267,642, filed on May 1, 2014, now Pat. No. 9,649,031.

(51) Int. Cl.

| | |
|---|---|
| *G06T 7/64* | (2017.01) |
| *A61B 3/14* | (2006.01) |
| *A61B 3/10* | (2006.01) |
| *A61B 3/12* | (2006.01) |
| *G06T 7/00* | (2017.01) |

(52) U.S. Cl.
CPC ............... *A61B 3/12* (2013.01); *A61B 3/14* (2013.01); *G06T 7/0012* (2013.01); *G06T 7/64* (2017.01); *G06T 2207/30041* (2013.01)

(56) References Cited

U.S. PATENT DOCUMENTS

| | | | |
|---|---|---|---|
| 7,219,997 | B2 | 5/2007 | Yokota et al. |
| 8,194,936 | B2 | 6/2012 | Abramoff et al. |
| 8,422,750 | B2 | 4/2013 | Atkinson et al. |
| 9,039,183 | B2 | 5/2015 | Muyo et al. |
| 2004/0080712 | A1 | 4/2004 | Yokota et al. |
| 2006/0087615 | A1 | 4/2006 | Kojima et al. |
| 2009/0175525 | A1 | 7/2009 | Farrer et al. |
| 2010/0150415 | A1* | 6/2010 | Atkinson ............. A61B 3/1225 382/128 |
| 2011/0311109 | A1 | 12/2011 | Demarais et al. |
| 2014/0107960 | A1 | 4/2014 | Oritz Egea et al. |

OTHER PUBLICATIONS

Bondiau, "Automatic three-dimensional model for protontherapy of the eye: preliminary results" (Year: 2003).*

Office Action from Japanese Pat. Appln. No. 2019-005172, dated Dec. 10, 2019.

Dobler et al., "Precise modeling of the eye for proton therapy of intra-ocular tumours", Physics in Medicine and Biology, nstitute of Physics Publfshing, vol. 47, No. 4, Feb. 2002, pp. 593-613.

Dolemeyer, Amo, "Fundus reconstruction by model-based rear projection," PhD Thesis, Jan. 26, 2005, 1-132 (with English Translation).

European Search Report issued in EP 14166786.5 dated Jun. 27, 2016.

Extended European Search Report issued in EP 14166786.5 dated Dec. 2, 2014.

Non-Final Rejection issued in U.S. Appl. No. 14/267,642 dated Sep. 14, 2016.

United Kingdom Office Action issued in GB1700162.9 dated Jul. 20, 2017.

United Kingdom Office Action issued in GB1407679.8 dated Oct. 13, 2014.

Yu ping et al., "Retinal image registration from 2d to 30" Computer Vision and Pattern Recognition, 208, IEEE Conference on IEE, Jun. 23, 2008, pp. 1-8.

Lee et al., "Retinal atlas statistics from color fundus images", Proc. SPIE 7623, Medical Imaging 2010: Image Processing, 762310 (Mar. 12, 2010).

Bondiau et al., "Automatic three-dimensional model for protontherapy of the eye: preliminary results", Med. Phys. 30, 6 . . . , Jun. 2003.

T. Vicentry, Direct and Inverse Solutions of Geodesics on the Ellipsoid with Application of Nested Equations, DMAAC Geodetic Survey Squadron, Survey Review XXIII, Apr. 1975, vol. 23, Issue 176, pp. 88-93.

Notice of Reasons for Refusal dated Jul. 13, 2021 issued in relation to the corresponding Japanese application 2020-151496 (Japanese version: 3 sheets; English translation attached; 6 sheets).

\* cited by examiner

Fig. 1

Fig. 2

IMAGING OF THE EYE

RELATED APPLICATION

This application is a continuation of U.S. application Ser. No. 15/484,935, filed Apr. 11, 2017, which is a continuation of U.S. application Ser. No. 14/267,642, filed May 1, 2014, which claims benefit of Application No. 1307990.0 filed on May 2, 2013 in the United Kingdom, and which applications are incorporated herein by reference. To the extent appropriate, a claim of priority is made to each of the above disclosed applications.

FIELD OF THE DISCLOSURE

The present application relates to improvements in and relating to imaging of the eye, particularly determining geometrical measurements of the eye.

BACKGROUND

There are various types of imaging devices which may be used to obtain images of an eye, for example ophthalmoscopes and fundus cameras. Specifically, such devices take measurements of the retina of the eye, which is a three dimensional structure approximated by a sphere. The output of the imaging devices is a two dimensional image of the three dimensional retina, as two dimensional images have a number of advantages, not least that they are able to be represented on a computer screen and output as photographs etc. The imaging devices inspect, e.g. scan, the three dimensional retina and produce two dimensional images of the retina. In inspecting the three dimensional retina, the devices introduce distortion, which distortion is determined by the optical and mechanical properties of the devices. The distortion compromises one or more properties of the two dimensional images of the retina, for example distance, area and angle preservation. If geometrical measurements of a retina are required, such as the distance between two structures of the retina, and these are made using a two dimensional image produced by such imaging devices, the results will be distorted and inaccurate.

SUMMARY

According to a first aspect of the present solution there is provided a method of determining a geometrical measurement of a retina of an eye, comprising
(i) obtaining a two dimensional representation of at least a portion of the retina of the eye,
(ii) deriving a geometrical remapping which converts the two dimensional representation of the retinal portion to a three dimensional representation of the retinal portion,
(iii) using one or more coordinates of the two dimensional representation of the retinal portion to define the geometrical measurement to be taken of the retina on the two dimensional representation,
(iv) using the geometrical remapping to convert the or each coordinate of the two dimensional representation of the retinal portion to an equivalent coordinate of the three dimensional representation of the retinal portion, and
(v) using the or each equivalent coordinate of the three dimensional representation of the retinal portion to determine the geometrical measurement of the retina of the eye.

Deriving the geometrical remapping which converts the two dimensional representation of the retinal portion to a three dimensional representation of the retinal portion may comprise determining a correction for distortion introduced into the two dimensional representation of the retinal portion in production thereof. Distortion may be introduced into the two dimensional representation of the retinal portion in production thereof by optical and mechanical properties of an imaging device used to produce the two dimensional representation.

Determining the correction for distortion in the two dimensional representation may comprise modelling the optical and mechanical properties of the imaging device.

Modelling the optical and mechanical properties of the imaging device may comprise
(i) constructing an optical description of an imaging system comprising the imaging device and a model eye,
(ii) passing a ray through the imaging system onto a retinal surface of the model eye,
(iii) calculating an actual measurement of the ray at the retinal surface, (iv) determining a horizontal scanning angle and a vertical scanning angle of the imaging system for the ray,
(v) calculating an expected measurement of the ray at the retinal surface using the horizontal scanning angle and vertical scanning angle of the imaging system,
(vi) repeating steps (ii) to (v) for a plurality of further rays, and
(vii) comparing the actual measurements of the rays at the retinal surface with corresponding expected measurements of the rays at the retinal surface to determine the correction for distortion in eye representations of the imaging device.

Constructing an optical description of the imaging system comprising the imaging device and the model eye may comprise determining optical path properties of the imaging device, determining optical path properties of the model eye and concatenating the optical path properties to give optical path properties of the imaging system. Determining the optical path properties of the imaging device may comprise ascertaining components of the imaging device which have an optical path effect, ascertaining the order of the components in the imaging device, establishing a mathematical function describing the optical path properties over time of each component, concatenating in order the optical path properties of the components to give the optical path properties of the imaging device. Determining the optical path properties of the model eye may comprise ascertaining components of the model eye which have an optical path effect, ascertaining the order of the components in the model eye, establishing a mathematical function describing the optical path properties of each component, concatenating in order the optical path properties of the components to give the optical path properties of the model eye.

Passing the rays through the imaging system onto the retinal surface of the model eye may comprise using a ray tracing system. The ray tracing system may be a commercially available ray tracing system such as Zemax. Using the ray tracing system may comprise loading the optical description of the imaging system into the ray tracing system and determining a path through the imaging system for each of the rays. Calculating the actual measurement of each ray at the retinal surface may comprise calculating coordinates of a point of intersection of each ray with the retinal surface.

Determining the horizontal scanning angle for a ray may comprise ascertaining an angular position of a horizontal scanning element of the imaging device used to produce the ray and using this to calculate the horizontal scanning angle for the ray. Determining the vertical scanning angle of the system for a ray may comprise ascertaining an angular position of a vertical scanning element of the imaging device used to produce the ray and using this to calculate the vertical scanning angle for the ray.

Calculating the expected measurement of each ray at the retinal surface may comprise using the horizontal scanning angle and the vertical scanning angle of the imaging system to calculate coordinates of a point of intersection of each ray with the retinal surface.

Determining the correction for distortion in eye representations of the imaging device may comprise deriving an analytical transformation that maps the actual measurements of the rays at the retinal surface of the model eye onto the corresponding expected measurements of the rays at the retinal surface of the model eye. Determining the correction for distortion in eye representations of the imaging device may comprise constructing a correction look up table (LUT) comprising, for each of a plurality of rays, an actual location of the ray at the retinal surface of the model eye against an expected location of the ray at the retinal surface of the model eye.

The method of determining the correction for distortion in the two dimensional representation may further comprise determining the correction for distortion in eye representations of the imaging device for a plurality of non-zero gaze angles of the model eye. For each non-zero gaze angle, this may further comprise measuring the gaze angle using a fovial location of the model eye. A correction LUT may be constructed for each of the plurality of non-zero gaze angles.

Determining the correction for distortion in the two dimensional representation may comprise
(i) creating a target,
(ii) computing an image of the target,
(iii) using an imaging device used to produce the two dimensional representation to scan the target to create a distorted image of the target, and
(iv) comparing the computed image of the target with the distorted image of the target to determine the correction for image distortion of the imaging device.

Computing the image of the target may comprise calculating coordinates of a plurality of points of the image of the target. Scanning the target may comprise passing a plurality of rays through the imaging device to determine coordinates of a plurality of points of the distorted image of the target.

Comparing the computed image of the target with the distorted image of the target may comprise comparing points of the computed image of the target with corresponding points of the distorted image of the target.

Determining the correction for image distortion of the imaging device may comprise deriving an analytical transformation that maps coordinates of points of the distorted image of the target onto coordinates of corresponding points of the computed image of the target. Determining the correction for image distortion of the imaging device may comprise constructing a correction look up table comprising, for each of a plurality of possible points of the distorted image of the target, coordinates of the possible point of the distorted image against coordinates of the corresponding point of the computed image of the target.

The target may comprise a plurality of contrasting shapes. The target may have a predefined pattern on it.

Determining the correction for distortion in the two dimensional representation may comprise receiving an image of an eye and transforming the image until it substantially registers with an image of the eye produced by an imaging device for which distortion correction is already known.

Determining the correction for distortion in the two dimensional representation may comprise a third party determining the correction and receiving the correction from the third party.

The geometrical remapping which converts the two dimensional representation of the retinal portion to a three dimensional representation of the retinal portion may take the form of an analytic equation that transforms coordinates of the two dimensional representation into equivalent coordinates of the three dimensional representation. The geometrical remapping which converts the two dimensional representation of the retinal portion to a three dimensional representation of the retinal portion may take the form of a lookup table that lists coordinates of the two dimensional representation equivalent to coordinates of the three dimensional representation. The coordinates of the three dimensional representation may be Cartesian coordinates or may be spherical coordinates The one or more coordinates of the two dimensional representation of the retinal portion used to define the geometrical measurement may define one or more points on the two dimensional representation. The or each point on the two dimensional representation may be identified using a Cartesian coordinate space. The or each point on the two dimensional representation may be identified on a screen using a pointing device such as a mouse.

Using the geometrical remapping to convert one or more coordinates of the two dimensional representation of the retinal portion to an equivalent coordinate of the three dimensional representation of the retinal portion may comprise using the geometrical remapping to map coordinates of one or more point of the two dimensional representation into coordinates of one or more equivalent point of the three dimensional representation.

The or each equivalent coordinate of the three dimensional representation of the retinal portion may comprise one or more points on the three dimensional representation. The or each point on the three dimensional representation may be identified using a Cartesian coordinate space. The or each point on the three dimensional representation may be identified using a spherical coordinate space.

The geometrical measurement of the retinal portion may comprise a distance measurement of a structure of the retinal portion. The distance geometrical measurement may be defined on the two dimensional representation of the retinal portion using coordinates of first and second points of the two dimensional representation. The geometrical remapping may be used to convert the first and second points of the two dimensional representation of the retinal portion to equivalent first and second points of the three dimensional representation of the retinal portion. Using the equivalent first and second points of the three dimensional representation to determine the distance geometrical measurement may comprise using the first point of the three dimensional representation to define a start position of the measurement and using the second point of the three dimensional representation to define a finish position of the measurement and measuring the distance between the first point and the second point of the three dimensional representation. The three dimensional representation of the retinal portion may be considered to be a sphere and the distance between the first point and the second point measured as the shortest distance between the first and second points of the sphere.

The shortest distance between the first and second points on the sphere may be measured in units relative to the sphere (degrees or radians) using a spherical law of cosines method namely $$\Delta \sigma = \arccos(\sin \phi_s \sin \phi_f + \cos \phi_s \cos \phi_f \cos \Delta \lambda)$$

where $\Delta\sigma$ is the central angle between the points, $\lambda_s$, $\phi_s$ and $\lambda_f$, $\phi_f$ is the longitude and latitude respectively of the first and second points and $\Delta\lambda$ is the absolute difference of the longitudes.

The shortest distance between the first and second points on the sphere measured in units relative to the sphere may be converted into physical units (mm) using $$d = r\Delta\sigma$$

where d is the distance between the points, r is the radius of the sphere and $\Delta\sigma$ is the central angle between the points and is given in radians.

The shortest distance between the first and second points on the sphere may be measured in units relative to the sphere (degrees or radians) using Vincenty formulae namely $$\Delta\sigma = \arctan\left(\frac{\sqrt{(\cos\phi_f \sin\Delta\lambda)^2 + (\cos\phi_s \sin\phi_f - \sin\phi_s \cos\phi_f \cos\Delta\lambda)^2}}{\sin\phi_s \sin\phi_f + \cos\phi_s \cos\phi_f \cos\Delta\lambda}\right)$$

where $\Delta\sigma$ is the central angle between the points, $\lambda_s$, $\phi_s$ and $\lambda_f$, $\phi_f$ is the longitude and latitude respectively of the first and second points and $\Delta\lambda$ is the absolute difference of the longitudes.

The shortest distance between the first and second points on the sphere measured in units relative to the sphere may be converted into physical units (mm) using $$d = r\Delta\sigma$$

where d is the distance between the points, r is the radius of the sphere and $\Delta\sigma$ is the central angle between the points and is given in radians.

The distance geometrical measurement may be output to a user. The distance geometrical measurement may be represented on the two dimensional representation of the retinal portion. The shortest distance between the first and second points on the three dimensional sphere (geodesic) will not necessarily correspond to a straight line on the two dimensional representation of the retinal portion. Representing the distance geometrical measurement on the two dimensional representation may comprise parameterising the distance between the first and second points on the sphere, calculating a plurality of intermediate points and using the points to represent the distance geometrical measurement on the two dimensional representation.

The geometrical measurement of the retinal portion may comprise an angle between first and second structures of the retinal portion. The angle geometrical measurement may be defined on the two dimensional representation of the retinal portion using coordinates of a first point and a second point of the two dimensional representation to mark the first structure and using coordinates of the first point and a third point of the two dimensional representation to mark the second structure. The geometrical remapping may be used to convert the first, second and third points of the two dimensional representation of the retinal portion to equivalent first, second and third points of the three dimensional representation of the retinal portion. Using the equivalent points of the three dimensional representation to determine the angle geometrical measurement may comprise using the first point and the second point of the three dimensional representation to mark the first structure and using the first point and the third point of the three dimensional representation to mark the second structure and measuring the angle between the second point and the third point through the first point in the three dimensional representation. The angle, C, may be measured using the law of haversines, namely $$\mathrm{haversin}(c) = \mathrm{haversin}(a-b) + \sin(a)\sin(b)\mathrm{haversin}(C)$$

where $\mathrm{haversin}(x) \equiv \sin^2(x/2)$, x1 and x2 are the first and second points on the three dimensional representation which mark the first structure, x1 and x3 are the points on the three dimensional representation which mark the second structure, a is the arclength of the geodesic between x1 and x2, b is the arclength of the geodesic between x1 and x3 and c is the arclength of the geodesic between x2 and x3.

The angle geometrical measurement may be output to a user. The angle geometrical measurement may be represented on the two dimensional representation of the retinal portion by representing sides of the angle (the geodesic between x1 and x2 and the geodesic between x1 and x3) on the two dimensional representation.

The geometrical measurement of the retinal portion may comprise an area of a structure of the retinal portion. The area geometrical measurement may be defined on the two dimensional representation of the retinal portion using coordinates of a plurality of points of the two dimensional representation. The geometrical remapping may be used to convert the plurality of points of the two dimensional representation of the retinal portion to an equivalent plurality of points of the three dimensional representation of the retinal portion. Using the equivalent plurality of points of the three dimensional representation to determine the area geometrical measurement may comprise using the plurality of points of the three dimensional representation to define a shape of the structure and measuring the area of the shape in the three dimensional representation. The three dimensional representation of the portion of the retina may be considered to be a sphere and the shape of the structure may be defined as a polygon, and the area of the polygon may be measured using $$A = r^2\left(\sum_{i=1}^{n} \alpha_i - (n-2)\pi\right)$$

where A is the area of the polygon, $\alpha_i$ for i=1, . . . , n are the n angles internal to the polygon and r is the radius of the sphere. This yields a result in physical units (e.g. mm$^2$ if r is given in mm). If $r^2$ is omitted in the above formula, a result is obtained in units relative to the sphere, in steradians (sr), the unit of solid angle.

Using the equivalent plurality of points of the three dimensional representation to determine the area geometrical measurement may comprise using a plurality of pixels on the three dimensional representation to define a shape of the structure and measuring the area of the shape by summing the areas of the pixels. The areas of the pixels on the three dimensional representation may be calculated by assuming each pixel is a polygon with four points, each point representing one corner of the pixel.

When the three dimensional representation of the portion of the retina is considered to be a sphere, the radius of the sphere can be determined by measuring the diameter of the eye. When the three dimensional representation of the portion of the retina is considered to be a sphere, the radius of the sphere can be set to the average radius of the human eye, which is approximately 12 mm. Even if the radius of the eye is not known or cannot be approximated, relative measurements with respect to the size of the sphere of the retina may be made by assuming the eye is a unit-sphere. Distances on the sphere may be measured in radians or degrees and areas in steradians or square degrees.

Obtaining the two dimensional representation of at least a portion of the retina of the eye may comprise operating an imaging device to produce the two dimensional representation. Obtaining the two dimensional representation of at least a portion of the retina of the eye may comprise receiving a two dimensional representation already produced by an imaging device.

Obtaining the two dimensional representation of at least a portion of the retina of the eye may comprise receiving a distortion-corrected three dimensional representation of the retinal portion and using a projection to obtain the two dimensional representation from the three dimensional representation. The projection may be chosen from a plurality of known projections. The projection may be any of a conformal projection, preserving angles in the two dimensional representation, an equidistant projection, preserving distances in the two dimensional representation, an area-preserving projection, preserving areas in the two dimensional representation. Deriving the geometrical remapping which converts the two dimensional representation of the retinal portion to a three dimensional representation of the retinal portion may comprise determining an inverse of the projection used in obtaining the two dimensional representation of the retinal portion.

According to a second aspect of the present solution there is provided a computer readable non-transitory media storing program instructions which, when executed, perform a method of determining a geometrical measurement of a retina of an eye, comprising
(i) obtaining a two dimensional representation of at least a portion of the retina of the eye,
(ii) deriving a geometrical remapping which converts the two dimensional representation of the retinal portion to a three dimensional representation of the retinal portion,
(iii) using one or more coordinates of the two dimensional representation of the retinal portion to define the geometrical measurement to be taken of the retina on the two dimensional representation,
(iv) using the geometrical remapping to convert the or each coordinate of the two dimensional representation of the retinal portion to an equivalent coordinate of the three dimensional representation of the retinal portion, and
(v) using the or each equivalent coordinate of the three dimensional representation of the retinal portion to determine the geometrical measurement of the retina of the eye.

According to a third aspect of the present solution there is provided an imaging system for determining geometrical measurements of the retina of the eye, comprising
an imaging device which obtains a two dimensional representation of at least a portion of the retina of the eye,
a derivation element which derives a geometrical remapping which converts the two dimensional representation of the retinal portion to a three dimensional representation of the retinal portion,
a measurement definition element which uses one or more coordinates of the two dimensional representation of the retinal portion to define the geometrical measurement of the retina on the two dimensional representation,
a remapping element which uses the geometrical remapping to convert the or each coordinate of the two dimensional representation of the retinal portion to an equivalent coordinate of the three dimensional representation of the retinal portion, and
a measurement determination element which uses the or each equivalent coordinate of the three dimensional representation of the retinal portion to determine the geometrical measurement of the retina of the eye.

The measurement definition element may be provided as software or software and hardware in the imaging device. The derivation element, the remapping element and the measurement determination element may be provided as software in the imaging device.

The same eye imaged on different conventional imaging devices, will produce retinal representations that cannot directly be compared nor be overlaid. This is also true for same-eye representations produced by the same conventional imaging device, but with different gaze angles. In an embodiment of the present solution, once transformed into the three dimensional spherical representation, it is possible to measure retinal structures in physical units that are equivalent across imaging devices and therefore allow direct comparison and derivations of relationships. For example, measuring the distance between the centre of the optic nerve head and the fovea on two images of the same eye produced by different imaging devices should result in the same distance. Each imaging device will have a different distortion due to different optical and mechanical components as well as due to gaze angle during imaging. By measuring the distance in the same spherical representation it is possible to compensate for these differences.

The geometrical measurements of the portion of the retina of the eye may be used for:
classification of disease/trauma artefacts in the retinal portion,
comparison of measurements of structures of the retinal portion across different imaging devices,
longitudinal tracking of geometrical changes (e.g., changes in size, direction, distance) in anatomical structures and pathologies in the retinal portion of the eye,
development of treatment planning based on the geometrical measurements,
direct delivery of treatment, such as photocoagulation, based on geometrical coordinates derived from the geometrical measurements,
creation of normative databases based on distribution of geometrical measurements of anatomical structures over populations.

BRIEF DESCRIPTION OF DRAWINGS

Embodiments of the present solution will now be described by way of example only, with reference to the accompanying drawings, in which.

DETAILED DESCRIPTION

Figure 1:
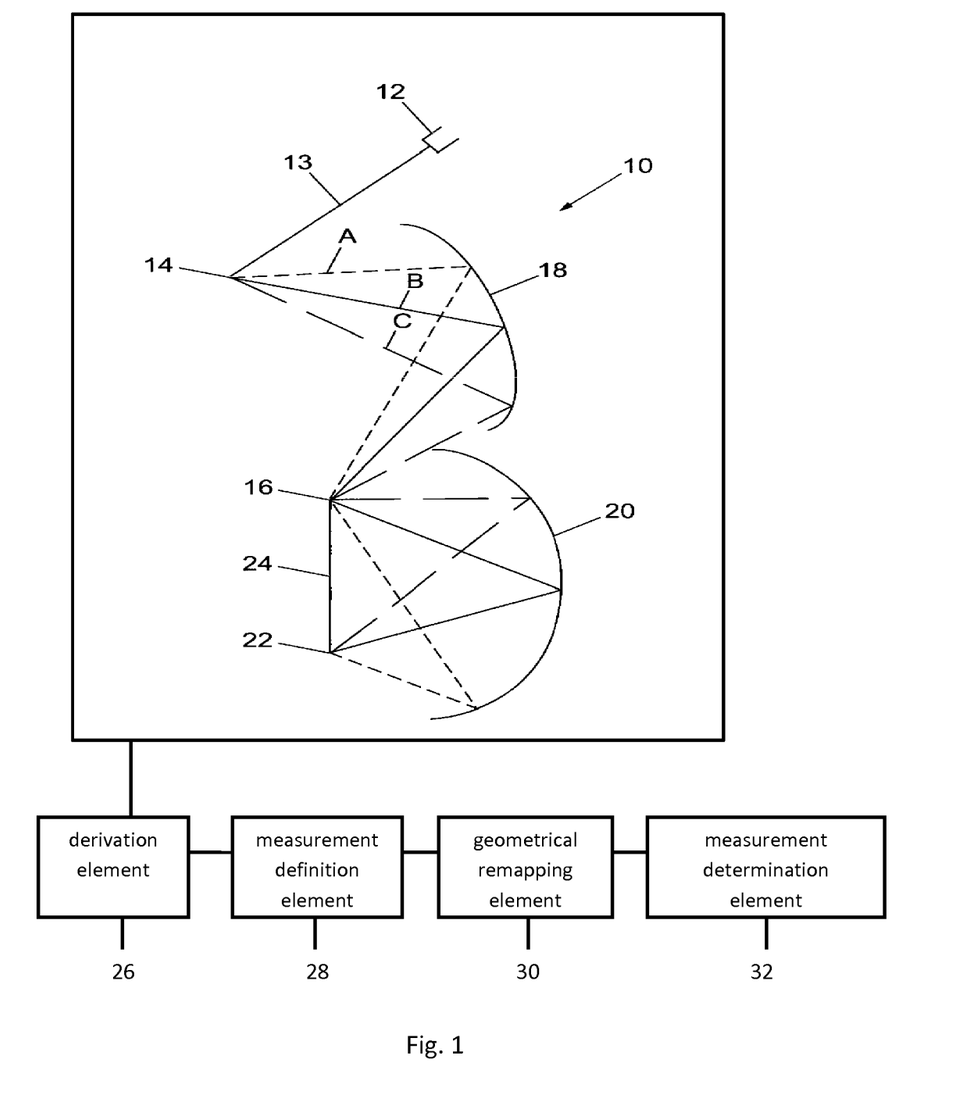
FIG. 1 is a schematic representation of an imaging system according to the third aspect of the present solution.

Referring to FIG. 1, the imaging system comprises an imaging device 10, a derivation element 26, a measurement definition element 28, a remapping element 30 and a measurement determination element 32. In this embodiment, the measurement definition element is provided as software and hardware, and the derivation element, the geometrical remapping element and the measurement determination element are provided as software in the imaging device.

The imaging device 10 comprises an ophthalmoscope. The ophthalmoscope comprises a light source 12 emitting a beam of light 13, scan relay elements comprising a first scanning element 14, a second scanning element 16, a scan compensation element 18 and a scan transfer element 20. The first scanning element 14 comprises a rotating polygon mirror and the second scanning element 16 comprises an oscillating plane mirror. The scan compensation element 18 comprises an ellipsoidal mirror and the scan transfer element 20 comprises an aspherical mirror.

The light source 12 directs an incident light beam 13 onto the first scanning element 14. This produces a scan of the beam (depicted by rays A, B and C) in a first, vertical, direction. The incident beam impinges on the scan compensation element 18 and is reflected from there onto the second scanning element 16. This produces a scan of the incident beam in a second, horizontal, direction. The incident beam then impinges on the scan transfer element 20, which has two foci, the second scanning element 16 is provided at a first focus and an eye 22 of a subject is provided at the second focus. The incident beam from the second scanning element 16 which impinges on the scan transfer element 20 will be directed to the eye 22 and will impinge on a portion of the retina of the eye. The light source 12 and the scan relay elements of the ophthalmoscope 10 combine to provide a two dimensional scan of the incident light beam 13 from an apparent point source and transfers the two dimensional scan of the incident light beam from the apparent point source to the retina of the eye. As the incident light beam is scanned over the retina, it will be reflected therefrom to produce a reflected light beam which is transmitted back through the elements of the ophthalmoscope 10 and received by one or more detectors (not shown). To acquire a representation of the portion of the retina of the subject's eye 22, the incident light beam from the source 12 is scanned over the retinal portion in a raster scan pattern, produced by the first and second scanning elements 14, 16 operating perpendicularly to each other and the reflected light beam received by the one or more detectors.

Figure 2:
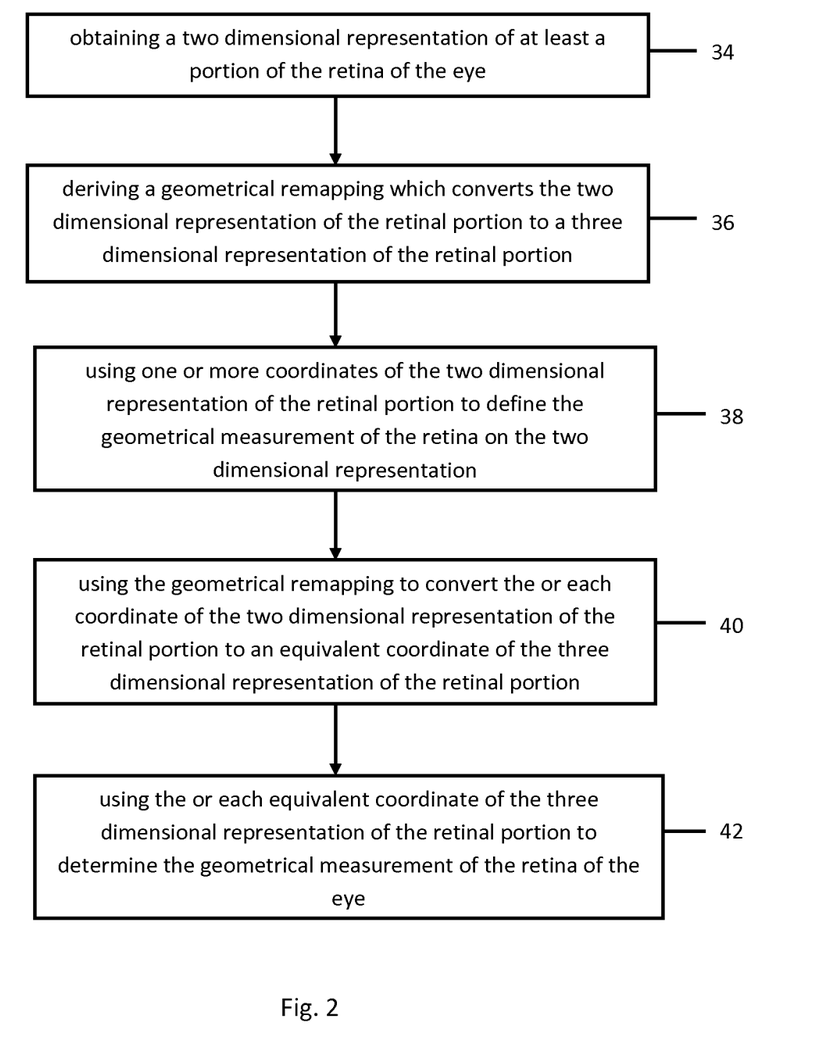
FIG. 2 is a flow chart illustrating the method according to the first aspect of the present solution.

Referring to FIGS. 1 and 2, the imaging device 10 obtains a two dimensional representation of a portion of the three dimensional retina of the eye 22 (step 34). The derivation element 26 receives the two dimensional representation of the retinal portion and uses this to derive a geometrical remapping which converts the two dimensional representation of the retinal portion to a three dimensional representation of the retinal portion (step 36). Deriving the geometrical remapping comprises determining a correction for distortion introduced into the two dimensional representation of the retinal portion by optical and mechanical properties of an imaging device used to produce the two dimensional representation.

In a first embodiment, determining the correction for distortion in the two dimensional representation comprises modelling the optical and mechanical properties of the imaging device 10. This comprises the following steps. An optical description of an imaging system comprising the imaging device 10 and a model eye is first constructed. This comprises determining optical path properties of the imaging device 10, determining optical path properties of the model eye and concatenating the optical path properties to give optical path properties of the imaging system. Determining the optical path properties of the imaging device 10 comprises ascertaining components of the imaging device 10 which have an optical path effect, ascertaining the order of the components in the imaging device 10, establishing a mathematical function describing the optical path properties over time of each component, concatenating in order the optical path properties of the components to give the optical path properties of the imaging device 10. Determining the optical path properties of the model eye comprises ascertaining components of the model eye which have an optical path effect, ascertaining the order of the components in the model eye, establishing a mathematical function describing the optical path properties of each component, concatenating in order the optical path properties of the components to give the optical path properties of the model eye.

The optical description of the imaging system is loaded into a ray tracing system, such as Zemax, a ray is passed through the imaging system onto a retinal surface of the model eye and a path through the imaging system for the ray is determined. An actual measurement of the ray at the retinal surface is calculated as coordinates of a point of intersection of the ray with the retinal surface.

A horizontal scanning angle and a vertical scanning angle of the imaging system for the ray is then determined. This comprises ascertaining an angular position of a horizontal scanning element of the imaging device used to produce the ray and using this to calculate the horizontal scanning angle for the ray and ascertaining an angular position of a vertical scanning element of the imaging device used to produce the ray and using this to calculate the vertical scanning angle for the ray.

An expected measurement of the ray at the retinal surface is calculated using the horizontal scanning angle and vertical scanning angle of the imaging system. This comprises using the horizontal scanning angle and the vertical scanning angle of the imaging system to calculate coordinates of a point of intersection of the ray with the retinal surface.

The above steps are then repeated for a plurality of further rays. The actual measurements of the rays at the retinal surface are compared with corresponding expected measurements of the rays at the retinal surface to determine the correction for distortion in eye representations of the imaging device 10. The distortion correction may take the form of an analytical transformation that maps the actual measurements of the rays at the retinal surface of the model eye onto the corresponding expected measurements of the rays at the retinal surface of the model eye, or a correction look up table (LUT) comprising, for each of a plurality of rays, an actual location of the ray at the retinal surface of the model eye against an expected location of the ray at the retinal surface of the model eye. Determining the distortion correction may further comprise determining the distortion correction for a plurality of non-zero gaze angles of the model eye.

In a second embodiment, determining the correction for distortion in the two dimensional representation comprises the following steps. A target is firstly created comprising a plurality of contrasting shapes. An image of the target is then computed. The imaging device 10 used to produce the two dimensional representation is used to scan the target to create a distorted image of the target. Finally the computed image of the target is compared with the distorted image of the target to determine the correction for image distortion of the imaging device 10.

The distortion correction is then used to derive the geometrical remapping which converts the two dimensional representation of the retinal portion to the three dimensional representation of the retinal portion. The geometrical remapping takes the form of an analytic equation that maps coordinates of the two dimensional representation into equivalent coordinates of the three dimensional representation.

The two dimensional representation of the retinal portion is accessed by the measurement definition element 28 and a distance geometrical measurement is defined on the two dimensional representation of the retinal portion using coordinates of first and second points of the two dimensional representation (step 38). This comprises displaying the two dimensional representation of the retinal portion to a user, who identifies the first and second points on the two dimensional representation using a pointing device such as a mouse.

The remapping element 30 then uses the geometrical remapping to convert the first and second points of the two dimensional representation of the retinal portion to equivalent first and second points of the three dimensional representation of the retinal portion (step 40). This comprises using the transformation to map coordinates of the points of the two dimensional representation into coordinates of equivalent points of the three dimensional representation. The points on the three dimensional representation are identified using a spherical coordinate space.

The measurement determination element 32 then uses the equivalent first and second points of the three dimensional representation to determine the distance geometrical measurement (step 40). This comprises using the first point of the three dimensional representation to define a start position of the measurement and using the second point of the three dimensional representation to define a finish position of the measurement and measuring the distance between the first point and the second point of the three dimensional representation, which is the length of the structure of the retina of the eye 22. The three dimensional representation of the retinal portion is considered to be a sphere and the distance between the first point and the second point measured as the shortest distance between the first and second points of the sphere.

The shortest distance between the first and second points on the sphere is measured in units relative to the sphere (degrees or radians) using a spherical law of cosines method namely $$\Delta\sigma = \arccos(\sin \phi_s \sin \phi_f + \cos \phi_s \cos \phi_f \cos \Delta\lambda)$$

where $\Delta\sigma$ is the central angle between the points, $\lambda_s, \phi_s$ and $\lambda_f, \phi_f$ is the longitude and latitude respectively of the first and second points and $\Delta\lambda$ is the absolute difference of the longitudes.

The shortest distance between the first and second points on the sphere measured in units relative to the sphere may be converted into physical units (mm) using $$d = r\Delta\sigma$$

where d is the distance between the points, r is the radius of the sphere and $\Delta\sigma$ is the central angle between the points and is given in radians.

The distance geometrical measurement is represented on the two dimensional representation of the retinal portion, by parameterising the distance between the first and second points on the sphere, calculating a plurality of intermediate points and projecting the points to represent the distance geometrical measurement on the two dimensional representation. The distance geometrical measurement represented on the two dimensional representation of the retinal portion is then displayed to the user.

What is claimed:

1. A method of determining a distance geometrical measurement of a retina of an eye, the method comprising:
    obtaining a two dimensional representation of at least a portion of the retina of the eye, the at least a portion of the retina being a retinal portion;
    deriving a geometrical remapping which converts the two dimensional representation of the retinal portion to a three dimensional representation of the retinal portion;
    using a first coordinate and a second coordinate of the two dimensional representation of the retinal portion to define the distance geometrical measurement to be taken of the retina on the two dimensional representation;
    using the geometrical remapping to convert the first coordinate of the two dimensional representation of the retinal portion to an equivalent first coordinate of the three dimensional representation of the retinal portion;
    using the geometrical remapping to convert the second coordinate of the two dimensional representation of the retinal portion to an equivalent second coordinate of the three dimensional representation of the retinal portion;
    using the equivalent first coordinate and the equivalent second coordinate of the three dimensional representation of the retinal portion to determine, as the distance geometrical measurement of the retina of the eye, a shortest distance between the equivalent first coordinate and the equivalent second coordinate of the three dimensional representation of the retinal portion, and
    outputting the determined distance geometrical measurement to a user,
    wherein the determined distance geometrical measurement is represented on the two dimensional representation, and
    wherein the determined distance geometrical measurement is represented on the two dimensional representation by parameterizing the distance between the equivalent first coordinate and the equivalent second coordinate of the three dimensional representation, calculating a plurality of intermediate equivalent coordinates of the three dimensional representation, and using the equivalent coordinates to represent the distance geometrical measurement on the two dimensional representation.

2. The method of claim 1, wherein the three dimensional representation of the retinal portion comprises a sphere, and the equivalent first coordinate and the equivalent second coordinate of the three dimensional representation of the retinal portion are used to determine, as the distance geometrical measurement of the retina of the eye, a shortest distance between the equivalent first coordinate and the equivalent second coordinate of the sphere.

3. The method of claim 2, wherein the shortest distance between the equivalent first coordinate and the equivalent second coordinate of the sphere is determined based on a central angle between the equivalent first coordinate and the equivalent second coordinate.

4. The method of claim 3, wherein the shortest distance between the equivalent first coordinate and the equivalent second coordinate of the sphere is calculated as a product of a radius of the sphere and the central angle between the equivalent first coordinate and the equivalent second coordinate.

5. The method of claim 3, wherein the central angle between the equivalent first coordinate and the equivalent second coordinate is based on an absolute difference between a first longitude of the equivalent first coordinate and a second longitude of the equivalent second coordinate.

6. The method of claim 5, wherein the central angle, $\Delta\sigma$, between the equivalent first coordinate and the equivalent second coordinate is calculated using the following expression:

$$\Delta\sigma = \arccos(\sin\phi_s \sin\phi_f + \cos\phi_s \cos\phi_f \cos\Delta\lambda)$$

wherein $\phi_s$ is a latitude of the equivalent first coordinate, $\phi_f$ is a latitude of the equivalent second coordinate, and $\Delta\lambda$ is the absolute difference between the first longitude of the equivalent first coordinate and the second longitude of the equivalent second coordinate.

7. The method of claim 5, wherein the central angle, $\Delta\sigma$, between the equivalent first coordinate and the equivalent second coordinate is calculated using the following expression:

$$\Delta\sigma = \left( \frac{\sqrt{(\cos\varphi_f \sin\Delta\lambda)^2 + (\cos\varphi_2 \sin\varphi_f - \sin\varphi_s \cos\varphi_f \cos\Delta\lambda)^2}}{\sin\varphi_s \sin\varphi_f + \cos\varphi_s \cos\varphi_f \cos\Delta\lambda} \right)$$

wherein $\varphi_s$ is a latitude of the equivalent first coordinate, $\varphi_f$ is a latitude of the equivalent second coordinate, and $\Delta\lambda$ is the absolute difference between the first longitude of the equivalent first coordinate and the second longitude of the equivalent second coordinate.

8. The method of claim 1, wherein deriving the geometrical remapping comprises determining a correction for distortion introduced into the two dimensional representation of the retinal portion in production thereof.

9. The method of claim 8, wherein distortion is introduced into the two dimensional representation of the retinal portion by optical and mechanical properties of an imaging device used to produce the two dimensional representation, and determining the correction for distortion in the two dimensional representation comprises modelling the optical and mechanical properties of the imaging device.

10. The method of claim 9, wherein modelling the optical and mechanical properties of the imaging device comprises:
constructing an optical description of an imaging system comprising the imaging device and a model eye;
(ii) passing a ray through the imaging system onto a retinal surface of the model eye;
(iii) calculating an actual measurement of the ray at the retinal surface;
(iv) determining a horizontal scanning angle and a vertical scanning angle of the imaging system for the ray,
(v) calculating an expected measurement of the ray at the retinal surface using the horizontal scanning angle and vertical scanning angle of the imaging system,
(vi) repeating steps (ii) to (v) for a plurality of further rays, and
(vii) comparing actual measurements of the rays at the retinal surface with corresponding expected measurements of the rays at the retinal surface to determine correction for distortion in eye representations of the imaging device.

11. The method of claim 10, wherein determining the horizontal scanning angle for a ray comprises ascertaining an angular position of a horizontal scanning element of the imaging device used to produce the ray and using this to calculate the horizontal scanning angle for the ray.

12. The method of claim 10, wherein determining the vertical scanning angle of the system for a ray comprises ascertaining an angular position of a vertical scanning element of the imaging device used to produce the ray and using this to calculate the vertical scanning angle for the ray.

13. The method of any of claim 10, further comprising determining correction for distortion in eye representations of the imaging device for a plurality of non-zero gaze angles of the model eye.

14. The method of claim 9, wherein determining the correction for distortion in the two dimensional representation comprises:
creating a target;
computing an image of the target;
using an imaging device used to produce the two dimensional representation to scan the target to create a distorted image of the target; and
comparing the computed image of the target with the distorted image of the target to determine correction for image distortion of the imaging device.

15. An imaging system for determining a distance geometrical measurement of a retina of an eye, the imaging system comprising:
an imaging device configured to obtain a two dimensional representation of at least a portion of the retina of the eye, the at least a portion of the retina being a retinal portion; and
a processor and a memory storing computer program instructions which, when executed by the processor, cause the processor to:
derive a geometrical remapping which converts the two dimensional representation of the retinal portion to a three dimensional representation of the retinal portion;
use a first coordinate and a second coordinate of the two dimensional representation of the retinal portion to define the distance geometrical measurement to be taken of the retina on the two dimensional representation;
use the geometrical remapping to convert the first coordinate of the two dimensional representation of the retinal portion to an equivalent first coordinate of the three dimensional representation of the retinal portion;
use the geometrical remapping to convert the second coordinate of the two dimensional representation of the retinal portion to an equivalent second coordinate of the three dimensional representation of the retinal portion; and
use the equivalent first coordinate and the equivalent second coordinate of the three dimensional representation of the retinal portion to determine, as the distance geometrical measurement of the retina of the eye, a shortest distance between the equivalent first coordinate and the equivalent second coordinate of the three dimensional representation of the retinal portion, and
output the determined distance geometrical measurement to a user,
wherein the determined distance geometrical measurement is represented on the two dimensional representation, and
wherein the determined distance geometrical measurement is represented on the two dimensional representation by parameterizing the distance between the equivalent first coordinate and the equivalent second coordinate of the three dimensional representation, calculating a plurality of intermediate equivalent coordinates of the three dimensional representation, and using the equivalent coordinates to represent the distance geometrical measurement on the two dimensional representation.

16. The imaging system of claim 15, wherein the three dimensional representation of the retinal portion comprises a sphere, and the computer program instructions, when executed by the processor, cause the processor to use the equivalent first coordinate and the equivalent second coordinate of the three dimensional representation of the retinal portion to determine, as the distance geometrical measurement of the retina of the eye, a shortest distance between the equivalent first coordinate and the equivalent second coordinate of the sphere.

17. The imaging system of claim 16, wherein the computer program instructions, when executed by the processor, cause the processor to determine the shortest distance between the equivalent first coordinate and the equivalent second coordinate of the sphere based on a central angle between the equivalent first coordinate and the equivalent second coordinate.

18. The imaging system of claim 17, wherein the computer program instructions, when executed by the processor, cause the processor to calculate the shortest distance between the equivalent first coordinate and the equivalent second coordinate of the sphere as a product of a radius of the sphere and the central angle between the equivalent first coordinate and the equivalent second coordinate.

19. The imaging system of claim 17, wherein the central angle between the equivalent first coordinate and the equivalent second coordinate is based on an absolute difference between a first longitude of the equivalent first coordinate and a second longitude of the equivalent second coordinate.

20. The imaging system of claim 19, wherein the computer program instructions, when executed by the processor, cause the processor to calculate the central angle, $\Delta\sigma$, between the equivalent first coordinate and the equivalent second coordinate using the following expression:

$$\Delta\sigma = \arccos(\sin \phi_s \sin \phi_f + \cos \phi_s \cos \phi_f \cos \Delta\lambda)$$

wherein $\varphi_s$ is a latitude of the equivalent first coordinate, $\varphi_f$ is a latitude of the equivalent second coordinate, and $\Delta\lambda$ is the absolute difference between the first longitude of the equivalent first coordinate and the second longitude of the equivalent second coordinate.

21. The imaging system of claim 19, wherein the computer program instructions, when executed by the processor, cause the processor to calculate the central angle, $\Delta\sigma$, between the equivalent first coordinate and the equivalent second coordinate using the following expression:

$$\Delta\sigma = \left( \frac{\sqrt{(\cos\varphi_f \sin\Delta\lambda)^2 + (\cos\varphi_2 \sin\varphi_f - \sin\varphi_s \cos\varphi_f \cos\Delta\lambda)^2}}{\sin\varphi_s \sin\varphi_f + \cos\varphi_s \cos\varphi_f \cos\Delta\lambda} \right)$$

wherein $\varphi_s$ is a latitude of the equivalent first coordinate, $\varphi_f$ is a latitude of the equivalent second coordinate, and $\Delta\lambda$ is the absolute difference between the first longitude of the equivalent first coordinate and the second longitude of the equivalent second coordinate.

22. A computer-readable non-transitory storage medium storing computer program instructions which, when executed by a processor, cause the processor to determine a distance geometrical measurement of a retina of an eye by:
obtaining a two dimensional representation of at least a portion of the retina of the eye, the at least a portion of the retina being a retinal portion;
deriving a geometrical remapping which converts the two dimensional representation of the retinal portion to a three dimensional representation of the retinal portion;
using a first coordinate and a second coordinate of the two dimensional representation of the retinal portion to define the distance geometrical measurement to be taken of the retina on the two dimensional representation;
using the geometrical remapping to convert the first coordinate of the two dimensional representation of the retinal portion to an equivalent first coordinate of the three dimensional representation of the retinal portion;
using the geometrical remapping to convert the second coordinate of the two dimensional representation of the retinal portion to an equivalent second coordinate of the three dimensional representation of the retinal portion; and
using the equivalent first coordinate and the equivalent second coordinate of the three dimensional representation of the retinal portion to determine, as the distance geometrical measurement of the retina of the eye, a shortest distance between the equivalent first coordinate and the equivalent second coordinate of the three dimensional representation of the retinal portion, and
outputting the determined distance geometrical measurement to a user,
wherein the determined distance geometrical measurement is represented on the two dimensional representation, and
wherein the determined distance geometrical measurement is represented on the two dimensional representation by parameterizing the distance between the equivalent first coordinate and the equivalent second coordinate of the three dimensional representation, calculating a plurality of intermediate equivalent coordinates of the three dimensional representation, and using the equivalent coordinates to represent the distance geometrical measurement on the two dimensional representation.

23. The computer-readable non-transitory storage medium of claim 22, wherein the three dimensional representation of the retinal portion comprises a sphere, and the computer program instructions, when executed by a processor, cause the processor to use the equivalent first coordinate and the equivalent second coordinate of the three dimensional representation of the retinal portion to determine, as the distance geometrical measurement of the retina of the eye, a shortest distance between the equivalent first coordinate and the equivalent second coordinate of the sphere.

24. The computer-readable non-transitory storage medium of claim 23, wherein the computer program instructions, when executed by a processor, cause the processor to determine the shortest distance between the equivalent first coordinate and the equivalent second coordinate of the sphere based on a central angle between the equivalent first coordinate and the equivalent second coordinate.

25. The computer-readable non-transitory storage medium of claim 24, wherein the computer program instructions, when executed by a processor, cause the processor to calculate the shortest distance between the equivalent first coordinate and the equivalent second coordinate of the sphere as a product of a radius of the sphere and the central angle between the equivalent first coordinate and the equivalent second coordinate.

26. The computer-readable non-transitory storage medium of claim 24, wherein the central angle between the equivalent first coordinate and the equivalent second coordinate is based on an absolute difference between a first longitude of the equivalent first coordinate and a second longitude of the equivalent second coordinate.

27. The computer-readable non-transitory storage medium of claim 26, wherein the computer program instructions, when executed by a processor, cause the processor to calculate the central angle, $\Delta\sigma$, between the equivalent first coordinate and the equivalent second coordinate using the following expression:

$$\Delta\sigma = \arccos(\sin\phi_s \sin\phi_f + \cos\phi_s \cos\phi_f \cos\Delta\lambda)$$

wherein $\varphi_s$ is a latitude of the equivalent first coordinate, $\varphi_f$ is a latitude of the equivalent second coordinate, and $\Delta\lambda$ is the absolute difference between the first longitude of the equivalent first coordinate and the second longitude of the equivalent second coordinate.

28. The computer-readable non-transitory storage medium of claim 26, wherein the computer program instructions, when executed by a processor, cause the processor to calculate the central angle, $\Delta\sigma$, between the equivalent first coordinate and the equivalent second coordinate using the following expression:

$$\Delta\sigma = \left( \frac{\sqrt{(\cos\varphi_f \sin\Delta\lambda)^2 + (\cos\varphi_2 \sin\varphi_f - \sin\varphi_s \cos\varphi_f \cos\Delta\lambda)^2}}{\sin\varphi_s \sin\varphi_f + \cos\varphi_s \cos\varphi_f \cos\Delta\lambda} \right)$$

wherein $\varphi_s$ is a latitude of the equivalent first coordinate, $\varphi_f$ is a latitude of the equivalent second coordinate, and $\Delta\lambda$ is the absolute difference between the first longitude of the equivalent first coordinate and the second longitude of the equivalent second coordinate.

* * * * *